(12) United States Patent
Kopoian

(10) Patent No.: US 10,966,690 B2
(45) Date of Patent: Apr. 6, 2021

(54) SPECIMEN CONTAINER SYSTEM

(71) Applicant: Marc Kopoian, Scottsdale, AZ (US)

(72) Inventor: Marc Kopoian, Scottsdale, AZ (US)

( * ) Notice: Subject to any disclaimer, the term of this patent is extended or adjusted under 35 U.S.C. 154(b) by 255 days.

(21) Appl. No.: 15/890,313

(22) Filed: Feb. 6, 2018

(65) Prior Publication Data

US 2018/0280002 A1 Oct. 4, 2018

Related U.S. Application Data

(60) Provisional application No. 62/477,440, filed on Mar. 28, 2017.

(51) Int. Cl.

| | | |
|---|---|---|
| *A61B 10/00* | (2006.01) | |
| *B01L 3/00* | (2006.01) | |
| *B01L 9/00* | (2006.01) | |
| *G01N 37/00* | (2006.01) | |
| *A61B 5/00* | (2006.01) | |
| *G01N 1/18* | (2006.01) | |
| *G01N 1/20* | (2006.01) | |
| *G01N 21/00* | (2006.01) | |

(52) U.S. Cl.
CPC ............ *A61B 10/007* (2013.01); *B01L 3/508* (2013.01); *A61B 5/00* (2013.01); *A61B 10/00* (2013.01); *B01L 3/00* (2013.01); *B01L 9/00* (2013.01); *B01L 2200/0689* (2013.01); *B01L 2200/141* (2013.01); *B01L 2300/028* (2013.01); *B01L 2300/043* (2013.01); *B01L 2300/0851* (2013.01); *B01L 2300/0858* (2013.01); *G01N 1/18* (2013.01); *G01N 1/20* (2013.01); *G01N 21/00* (2013.01); *G01N 37/00* (2013.01)

(58) Field of Classification Search
CPC ......... A61B 10/007; A61B 5/00; A61B 10/00; A61B 10/0096; B01L 3/508; B01L 9/00; B01L 3/00; B01L 2300/028; B01L 2200/0689; B01L 2300/0851; B01L 2300/043; B01L 2300/0858; B01L 2200/141; B01L 3/5029; G01N 21/00; G01N 1/20; G01N 1/18; G01N 37/00; G01N 1/02

See application file for complete search history.

(56) References Cited

U.S. PATENT DOCUMENTS

| | | | |
|---|---|---|---|
| 4,064,760 A | 12/1977 | Benjamin | |
| 4,917,867 A * | 4/1990 | Jensen | ................. A61B 10/007 422/549 |
| 4,927,605 A | 5/1990 | Dorn et al. | |
| 5,119,830 A * | 6/1992 | Davis | ...................... B01L 3/502 422/568 |
| 5,913,435 A * | 6/1999 | Fuchs | ................ B65D 47/0814 215/235 |

(Continued)

*Primary Examiner* — Benjamin R Whatley
*Assistant Examiner* — Curtis A Thompson
(74) *Attorney, Agent, or Firm* — Knubox

(57) ABSTRACT

A specimen container system and methods of use are described herein for capturing, storing and accessing fluids for lab testing. A cup is removably secured to a cap assembly. The cap assembly is comprised of cover and a lid which are connected by a hinge assembly having a biasing member for maintain the lid in an open position. An aperture in the cap has two sections that in combination with the lid decreases the contamination risk compared to prior art container system.

17 Claims, 18 Drawing Sheets

(56) References Cited

U.S. PATENT DOCUMENTS

| | | | | |
|---|---|---|---|---|
| 6,054,099 | A * | 4/2000 | Levy | A61B 10/007 |
| | | | | 215/235 |
| 6,170,719 | B1 * | 1/2001 | Wilkinson | B01L 3/50825 |
| | | | | 215/235 |
| 6,171,261 | B1 * | 1/2001 | Niermann | A61B 10/0096 |
| | | | | 600/573 |
| 6,367,670 | B1 * | 4/2002 | Warner | B65D 47/0804 |
| | | | | 222/556 |
| 6,669,908 | B2 | 12/2003 | Weyker et al. | |
| 2002/0130100 | A1 * | 9/2002 | Smith | B01L 3/50825 |
| | | | | 220/259.1 |
| 2005/0074362 | A1 * | 4/2005 | Lappe | B01L 3/502 |
| | | | | 422/68.1 |
| 2006/0115385 | A1 * | 6/2006 | Jon Meyer | B01L 3/5635 |
| | | | | 422/547 |
| 2009/0242564 | A1 * | 10/2009 | Danks | B65D 47/0838 |
| | | | | 220/361 |
| 2010/0133285 | A1 * | 6/2010 | Schepen | B65D 21/0233 |
| | | | | 220/781 |
| 2011/0000137 | A1 * | 1/2011 | Druitt | B65D 47/0809 |
| | | | | 49/399 |
| 2012/0145710 | A1 * | 6/2012 | Corbett | B65D 77/06 |
| | | | | 220/9.4 |
| 2014/0105796 | A1 * | 4/2014 | Nagy | A61B 10/0096 |
| | | | | 422/550 |
| 2016/0003658 | A1 * | 1/2016 | Holden | G01F 11/268 |
| | | | | 222/1 |
| 2016/0199041 | A1 * | 7/2016 | Phillips | A61B 10/007 |
| | | | | 600/574 |
| 2017/0073115 | A1 * | 3/2017 | Crawford | B65D 47/06 |

* cited by examiner

SPECIMEN CONTAINER SYSTEM

CROSS REFERENCE TO RELATED APPLICATION

This application claims the benefit of U.S. provisional application Ser. No. 62/477,440 filed Mar. 28, 2017 by the present inventor, which is incorporated by reference in its entirety.

STATEMENT REGARDING FEDERALLY SPONSORED R&D

Not related to this application.

TECHNICAL FIELD

This invention relates to specimen collection containers, and more particularly to containers that minimizing potential contaminations in the collection, transporting and testing of urine.

BACKGROUND OF THE INVENTION

Specimen containers are well established and mature in the art of laboratory testing. Generally, specimen containers are used to hold and transport liquids, such as blood or urine, for testing.

Liquid specimen containers are typically made of plastic or glass and have a screw type cap. The cap or lid is removed by the patient or lab practitioner, and the open container is used for collecting a liquid for testing. With the correct amount of liquid in the container, the user or practitioner reseals the threaded cap to the container body. The container is used to transport the liquid to the desired test location, which may be near the collection location or at a remote laboratory. Prior to testing, a technician unscrews the cap from the container and extracts an amount of the contained fluid. Extraction methods include pouring from the container or extraction using an instrument, such as a pipette.

The greatest challenge in acquiring and transporting liquid samples for biological testing using prior art methods is contamination of the test fluid. There are many different types of tests that can be performed on biological liquid samples, and contamination of the fluid can produce false results. The testing of urine for colony counts is one such test that is susceptible to false results due to contamination. For example, a urine test may be performed to detect an infection of the urinary tract. The urine test is performed at the direction of doctors for determining the type and quantity of bacteria present in a patient. The quantity of bacteria is typically expressed as the number of colony forming units per unit volume of liquid (CFU per milliliter). The quantity may range from less than one-thousand to hundreds-of-thousands or more. The colony count is useful in predicting the severity of an infection. The type of bacteria present in the fluid is useful for determining an optimal treatment as certain types of bacteria require specialized antibiotics. Due to known likelihood of contaminations, a given test value is usually given with the test method performed. For example, a mid-stream urine collection method producing a test result of one-hundred-thousand CFU/ml may be considered significant, wherein a ten-thousand CFU/ml result may be considered significant if collected with a catheter. A catheter process is less prone to contamination than prior art mid-stream collection methods. While less accurate due to contamination risk, mid-stream collection is often used as a much less, costly, time consuming, and invasive process for the patient than catheter based collection processes. Contamination can be often identified as an odd test result, such as the presence of very high colony counts or the presence of multiple bacteria types. Typically, an odd result requires a second test to be performed. Multiple tests cause confusion, increased costs and delays in treating the patient.

Although urine tests, such as colony counts, are often used to test for non-life threatening diseases, a common misdiagnoses or delay in creating an accurate test result can cause an infection to spread to other parts of a patient's body, cause dangerous conditions like sepsis, and patient death. For improved patient health, it is desirable to create environments and test methods that result in low probabilities of test fluid contamination when utilizing a liquid specimen container in mid-stream collection processes.

Contamination can come from many sources during the collection, transport and testing of biological fluid samples. A first source is the accidental spillage of fluid on the outside of the cup during the collection process. A second source can come from sealing the specimen container after collection wherein cross-contamination can come from a user's or practitioner's hands. A third source is improperly sealed containers that exposed the fluid to external environments during transport. A fourth source is the opening of the container by the test technician, wherein they handle many cups in a day and their gloves and hands can cross-contaminate cups and fluids. A fifth source is spillage during opening a cup wherein fluid on a test surface can later contaminate hands, cups and withdrawal instruments. A sixth source is a container that accidentally tips during the test process causing large amount of fluid to spread, such an event can come from a pipette leaning at an angle within a container. A seventh source is drips from pouring fluid from a specimen container. Many more contamination sources are possible, and each is a risk to patient health.

There are numerous prior art containers for attempting to reduce the contamination of test fluids. One such prior art device is U.S. Pat. No. 5,119,830 to David, which is directed at a container that can be used for the collection, transport and testing of fluid without having to remove the fluid from the container. Although potentially useful to reduce contamination during testing, it is limited to test methods that can be placed into a cup. It does not solve the problem of reducing contaminations of cups used in typical test processes that involve extraction.

Another prior art device is U.S. Pat. No. 4,064,760 to Benjamin, which is directed at providing a removable funnel used in the collection process. While potentially useful to reduce contamination during collection, it introduces more handling, potential flow congestion, and an addition source for contamination.

Another prior art device is U.S. Pat. No. 4,927,605 to Dorn et al, which is directed at isolating a portion of the fluid within the collection container. While potentially useful to isolate a sample soon after collection, the additional components create new contamination sources, introduce increased cost and slow the test process.

Yet another prior art device is U.S. Pat. No. 6,669,908 to Weyker et al, which is directed at a container having a main chamber and subchamber which interfaces with a test device. While potentially useful to reduce exposure within the main chamber to contact with the test device and outside environment, it does not reduce contamination of fluid that must be poured or withdrawn for testing.

In addition to test fluids being susceptible to contamination, there are other drawbacks to prior art specimen collection containers. One such additional drawback is that lab technicians must repetitively unscrew caps from containers prior to testing. Repetitive motion, such as removing caps, is known to cause injuries and worker disabilities. Yet another drawback is that prior art containers can present a biological risk to testers wherein opening the container and withdrawing fluid can expose workers to infection diseases.

In these respects, the present invention departs from conventional concepts of the prior art by providing a specimen container system that is less likely to result in contamination and produce invalid test results. The present invention provides a low cost and simple way to reduce invalid test results of stored biological fluids utilizing common test methods.

SUMMARY OF THE INVENTION

The present invention takes a very different approach to reducing contamination of test fluids in comparison to the prior art.

The present invention provides a specimen container used for the collection, transport and testing of biological fluid samples. The specimen container has a cup, a cover and a lid. The cover is in threaded engagement with the cup and is connected to the lid. The cover, along with the lid can be removed from the cup during the collection process with little or no impact to existing practices. After collection, the cover and lid assembly are secured to the cup with little or no impact to existing practices. During transport, the lid, cover and cup maintain a fluid type seal. At the test location, the test technician flips open the lid exposing an aperture in the cover for removing an amount of fluid for testing. The technician may remove fluid by tilting the container and pouring, or may withdraw the fluid using instruments such as a pipette. After fluid is removed for testing, the test technician may simply close the lid to reduce risk of contamination and spillage of fluid remaining in the container.

The preferred embodiments of the present invention are directed at the collection, transport and testing of urine. Although urine is used to describe the best mode of the present invention, it should not be construed to be limited to such. Urine testing is used as an example fluid that is susceptible to environmental contamination which can yield unreliable test results. An unreliable test result often results in a retest which increases cost and risk to patient health. The present invention reduces the risk of contamination of urine with very little disruption to common test procedures and methods.

An object of the present invention is to create a specimen container that reduces the risk of test fluid contamination by allowing the fluid to be either poured, or withdrawn using an instrument, from an aperture of a cover that substantially covers the top of a cup. The aperture is comprised of a pour section and an access section, with each being optimally sized and shaped for their respective use. The aperture has a fluid tight flip lid that seals the fluid within the container system. One or more optional label configurations may contact a combination of the cover, lid, and cap.

An object of present invention is to create a specimen container optimally used for the collection, transport and testing of body fluids, such as blood or urine.

An object of the present invention is to create a specimen container that reduces the risk of contamination of the fluid by the outside environment.

An object of the present invention is to create a specimen container that reduces the risk of spillage during fluid testing.

An object of the present invention is to create a specimen container that provides access to a fluid by either pouring or extracting using a withdrawal instrument.

An object of the present invention is to create a specimen container that reduces the risk of repetitive motion injuries to test technicians.

Yet another object of the present invention is to create a specimen container that reduces the risk of a test technician becoming infected by a test fluid.

These and other features, aspects, and advantages of the present invention will become better understood about the following description, appended claims, and accompanying drawings.

BRIEF DESCRIPTION OF THE DRAWINGS

Preferred embodiments of the invention are described below with the reference to the following accompanying drawings:

FIG. 4 also shows an outside cup label, a lid label, and seal tape secured to the lid and cover.

FIG. 5 also shows a hinge assembly connecting the lid and cover.

FIG. 6 also shows the aperture of the cover and its pour and access sections. The lid is the bottom element shown.

DETAILED DESCRIPTION OF THE PREFERRED EMBODIMENTS

Some of the general components utilized in this invention are widely known and used in the field of the invention, and their exact nature or type is not necessary for a person of ordinary skill in the art or science to understand the invention; therefore, they will not be discussed in detail. In more detail, it is appreciated that generalized containers are well known in the art of laboratory testing and thus the exact features of threads, specimen testing and materials used are not needed for one to understand and practice the invention without undue experimentation, and thus will not be described in detail.

Capturing, storing and withdrawing of fluids, such as but not limited to urine or blood, is common in the art of laboratory testing and microbiological testing. A fluid may be captured from a patient and stored in a container, transported to a lab or test location, and then at least a portion of the fluid removed from the container for testing. The present invention is optimized for, but not limited to, colony count testing of urine. To achieve accurate test results, it is necessary that the fluids not be contaminated during the process of capturing, storing and withdrawing. Furthermore, many of the captured fluids are biologically hazardous and thus it is desirable for the container to minimize risk of spillage. For the purposes of teaching the best mode of the present invention, a process for capturing urine will be described. But, it should be appreciated that present invention is not limited to the process of urine testing or the exact process of urine testing as described herein. The present invention provides novel features that may be applied to any fluid testing where it is desirable to have low risk of contamination and cross-contamination.

Figure 1:
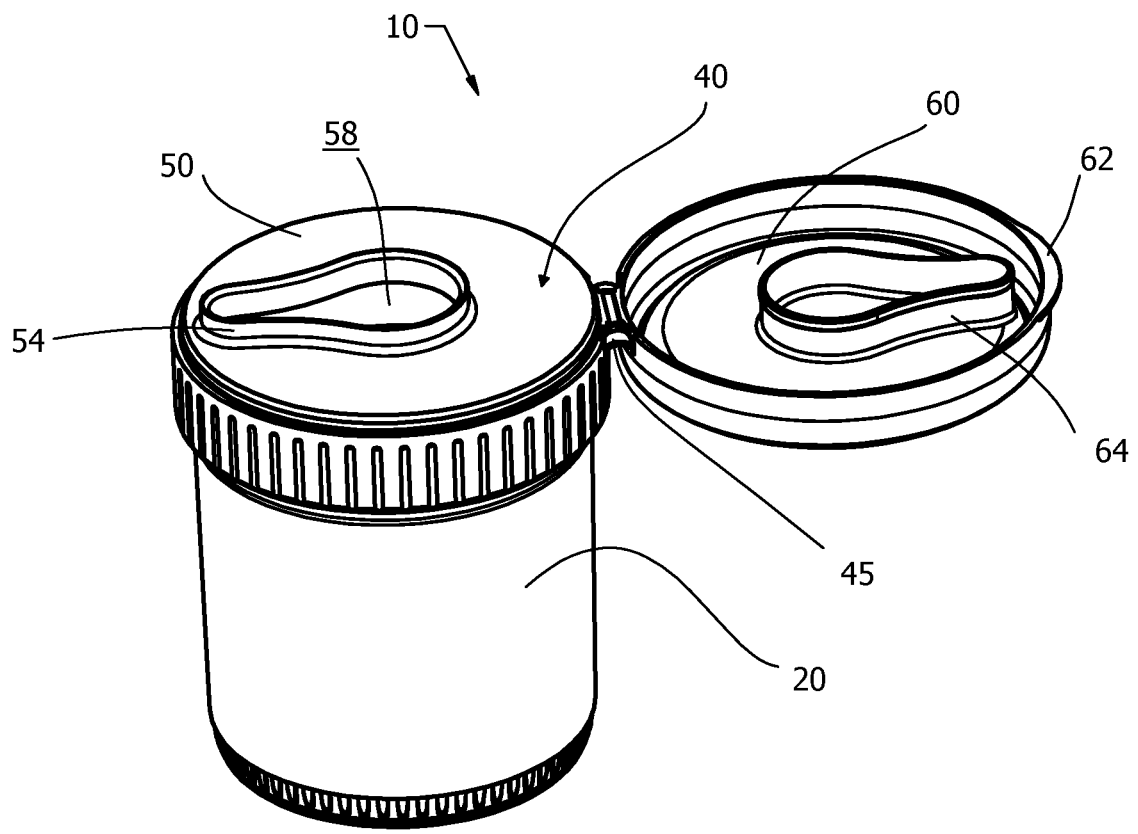
FIG. 1 is a front-top perspective view of a specimen container according to the present invention. The container is shown with a cup, a cover attached to the cup, and a lid in the open position.
Figure 2:
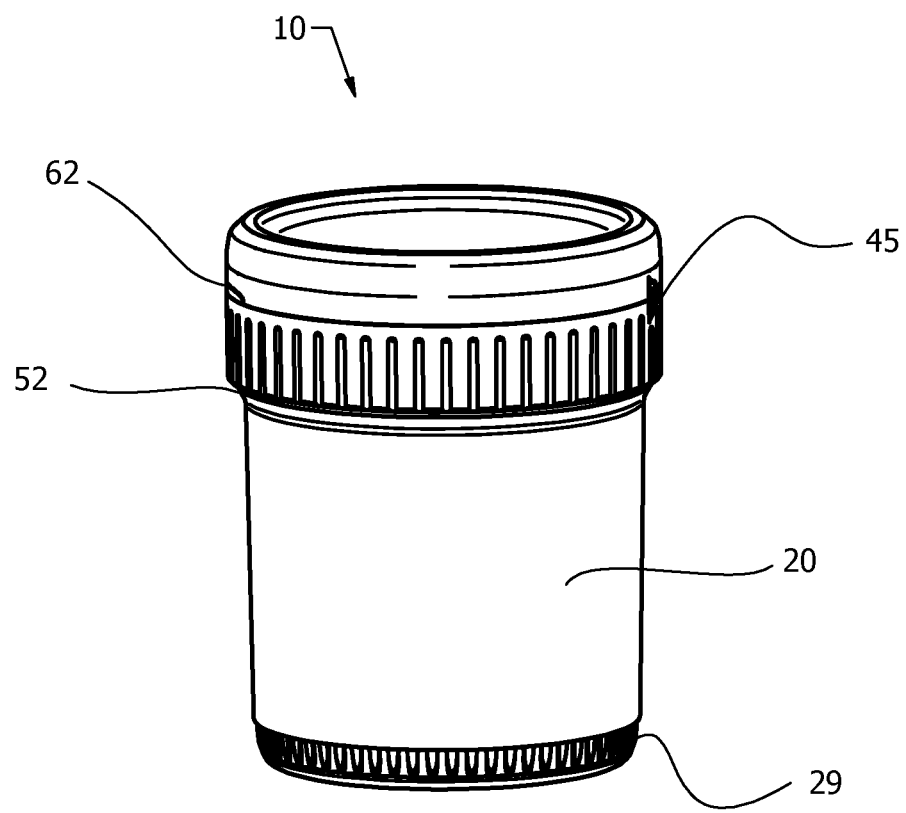
FIG. 2 is a back-top perspective view of the specimen container of FIG. 1 and showing the lid in the closed position.

Now referring to the drawings and according to the present invention, FIG. 1 shows a novel specimen container system 10. The novel features of specimen container system 10 will be described herein, and provides for reduced risk of cross-contamination and spillage of fluids stored within.

Figure 3:
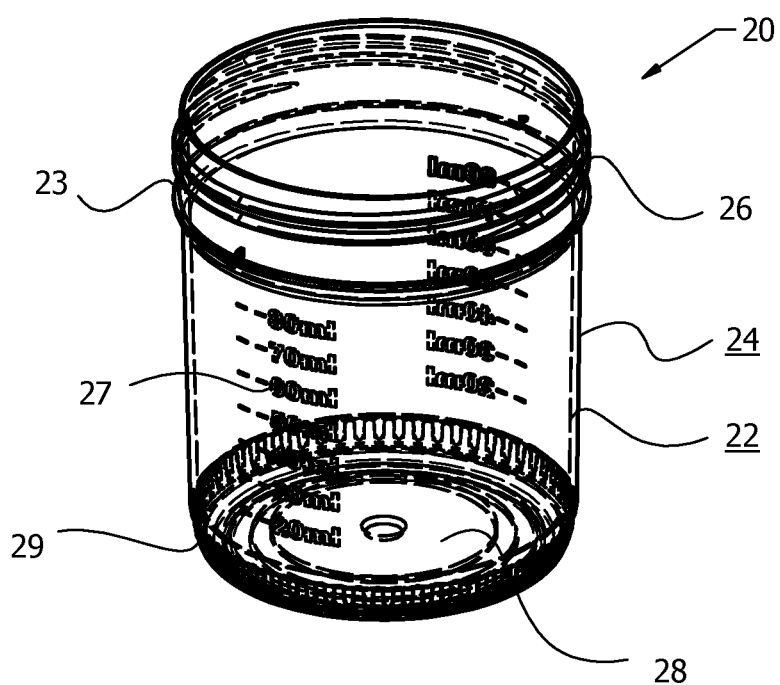
FIG. 3 is a top perspective view of the cup of FIG. 1 and showing the cup is preferably translucent. The cup has visible volume markings and threads at the top of its outer wall.

A cup 20 is shown attached to a cap assembly 40. Cup 20 is shown cylindrical, but may be any shape or size optimized for a process of capturing fluids. Cup 20 is shown optimized for capturing urine and has, but is not limited to, an approximate diameter of 50 mm. As shown in FIG. 3, cup 20 has a cup inner wall surface 22 an outer cup wall surface 24, and a base 28. At the top of outer cup wall surface 24 is a cup thread 26. Container threads are well known in the art of container design and the size and pitch may be selected from known industry standards. For urine storage, cup 20 is preferably made from polypropylene, or such material having low permeation and absorption properties to water. Cup 20 may also be made from glass or layers of bonded polymer materials each having optimal material properties for a given fluid. For proper testing, a certain amount of fluid may need to be captured, and an array of indicators 27 provide the ability to visually indicate the amount of liquid captured. As will be described later, cup 20 includes a cup shoulder 23 for interfacing with a holder 90. Cup 20 includes cup ridges 29 to reduce slippage between a user's hands and cup 20 during opening and closing, thus reducing potential spillage and contamination sources. Cup ridges 29 are depressions and ridges in the material that extend around cup 20.

Figure 5:
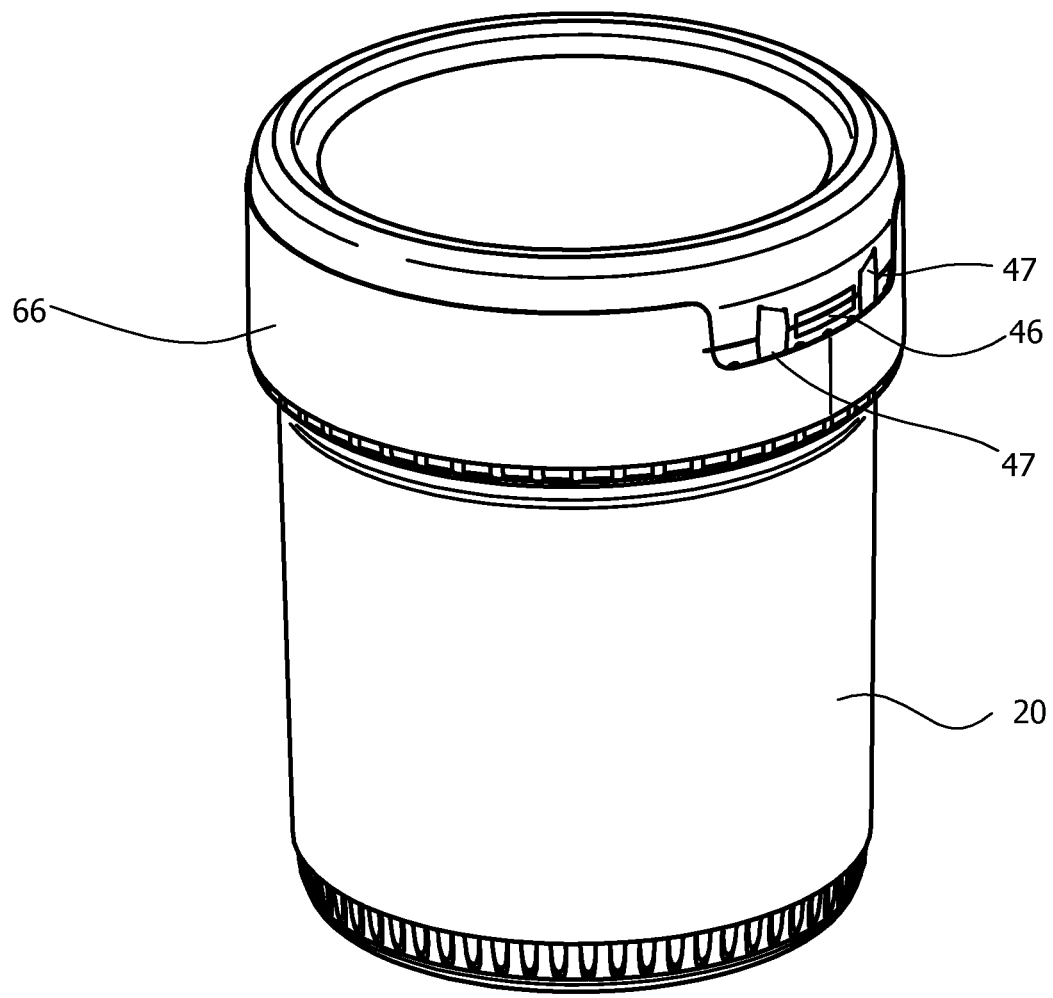
FIG. 5 is a top rear perspective view of the specimen container system of FIG. 2 with a seal tape in contact with the lid and cover.
Figure 7:
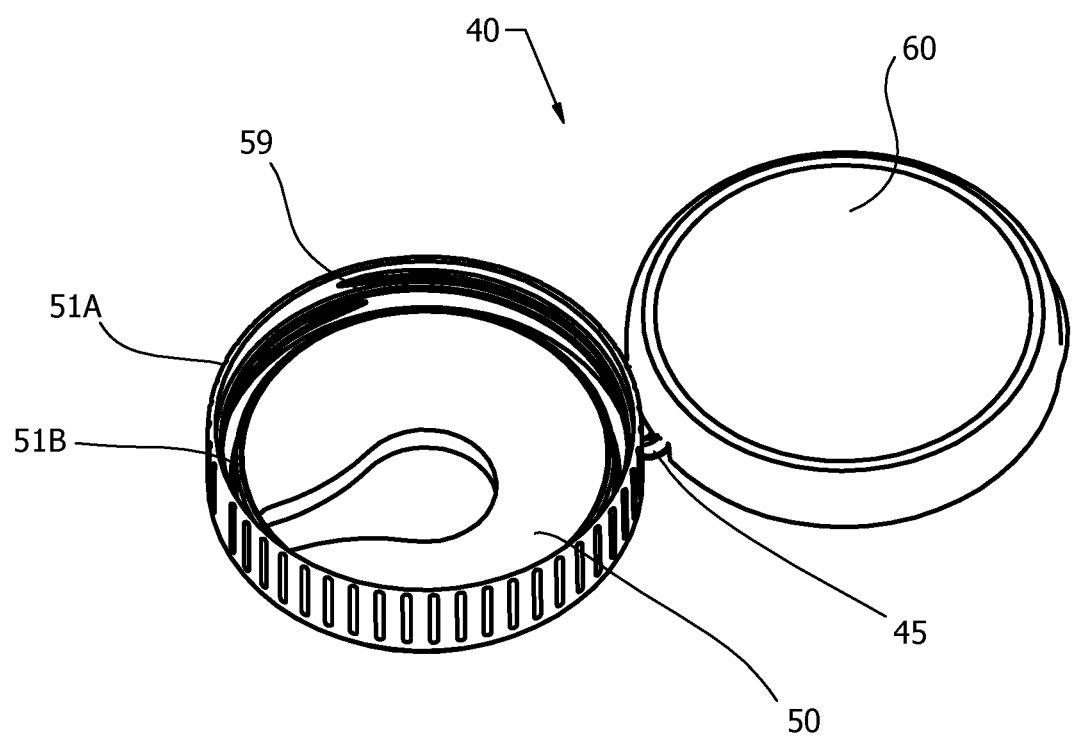
FIG. 7 is a perspective view of the cap assembly of FIG. 6 and showing the bottom of the cover and top of the lid in the open position.
Figure 11:
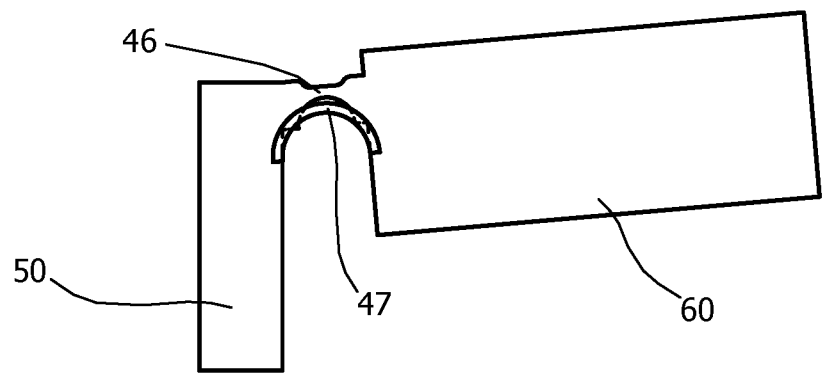
FIG. 11 is a side view diagram showing the bias bands between the cover and the lid in the open position.
Figure 12:
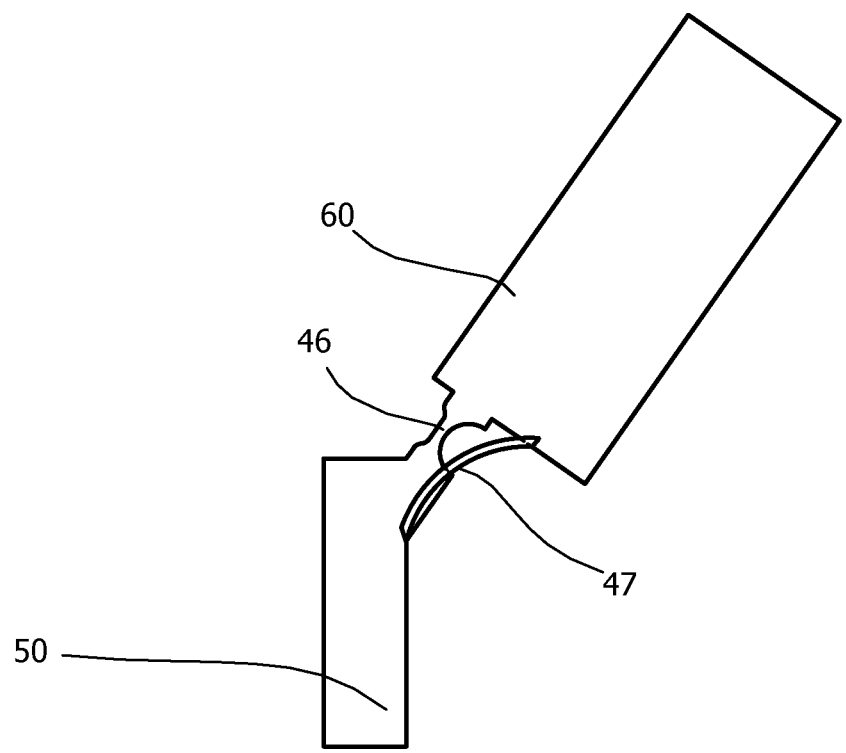
FIG. 12 is the same view as FIG. 11, but with the lid in the intermediate open position.
Figure 13:
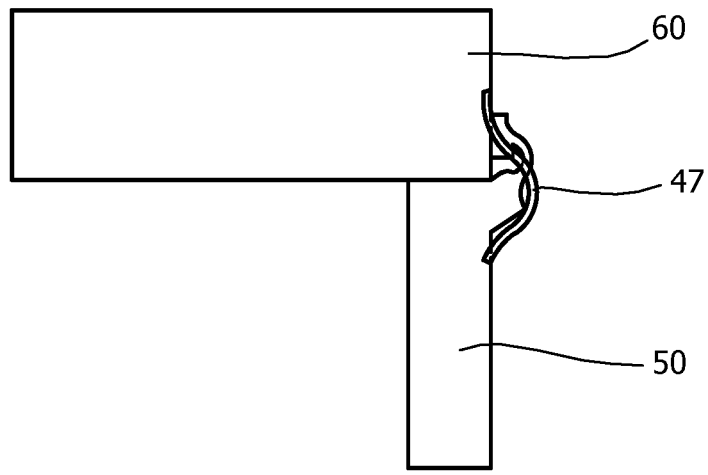
FIG. 13 is the same view as FIG. 11, but with the lid in the closed position.

As shown in FIG. 7, cap assembly 40 is comprised of a lid 60 and a cover 50. Preferably, securing lid 60 to cover 50 is hinge assembly 45. Similar to cup 20, cap assembly 40 is preferably made from polypropylene, but can be made from any material suitable for a particular application. As part of the best mode of the present invention, cap assembly 40 is molded as one piece which lowers production cost and ensures cover 50 is permanently connected to lid 60 by means of hinge assembly 45. Hinge 45 is preferably produced with a living-hinge 46 which has dimensions that allow it to be bendable in comparison to the rest of cap assembly 40. Although hinge 45 is described as a "living hinge", it should be appreciated that cap assembly 40 can be formed by two independent pieces with hinge 45 being created by snap features or bonded surfaces as part of cover 50 and lid 60. Furthermore, hinge assembly 45 preferably includes one or more bias bands 47. As shown in FIG. 7 and FIG. 11, with lid 60 in the open position, bias bands 47 are flexed in a neutral position. As shown in FIG. 12, as lid 60 moves to an intermediate position, bias bands 47 are slightly stretched and their respective connection points to lid 60 and cover 50 create a force to return lid 60 to the open position. This is accomplished by making a connection point of bias band 47 to both lid 60 and cover 50 below hinge 46 with lid 60 in the open position. The length, or arc-length, of bias band 47 can be altered to provide more or less return force. As will be described later, the one or more bands 47 provide the means to maintain lid 60 in the open position, thus reducing potential spillage and contamination of fluids. FIG. 13 and FIG. 5 show lid 60 in the closed position, which again causes bias bands 47 to bend and remain in a relaxed position.

Figure 8:
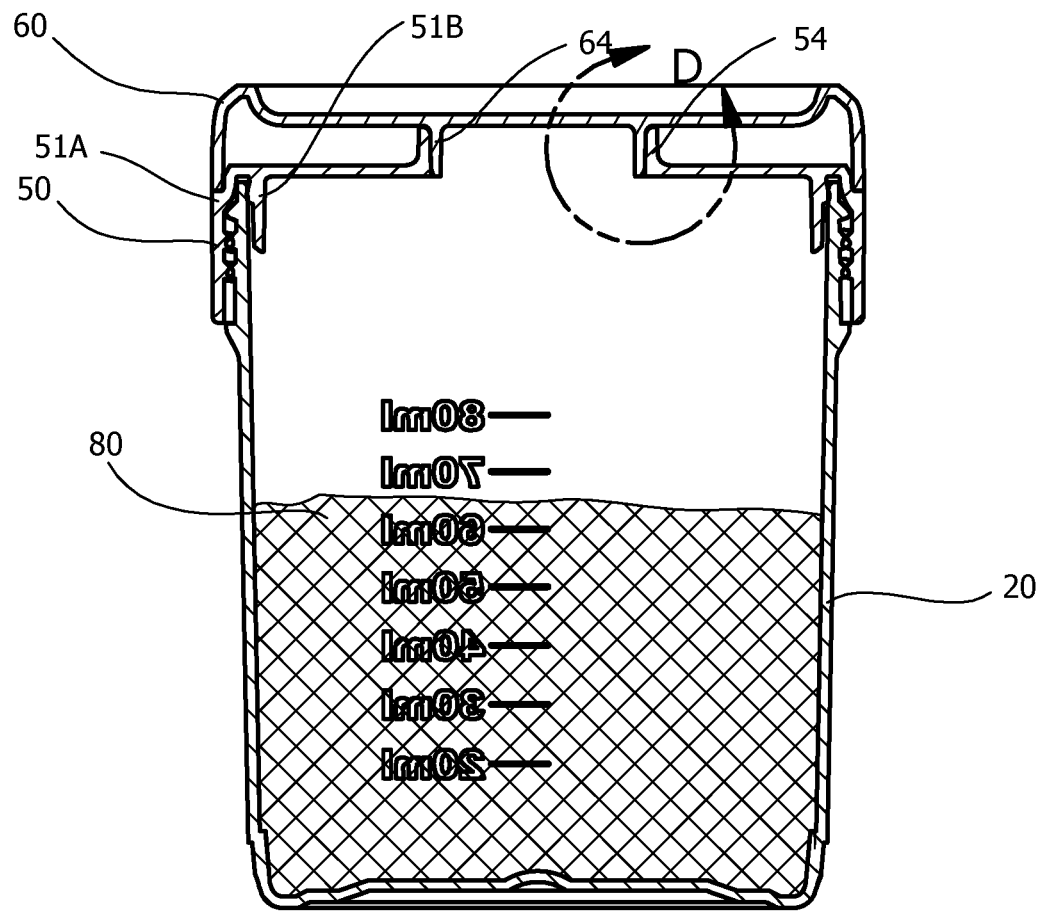
FIG. 8 is a side section view of the specimen container of FIG. 2 with the section starting at the mid-plane of the container system. The hatched section shows fluid within the cup.

Cover 50 is comprised of a cover inner wall 51B, a cover outer wall 51A and an aperture 58 which extends through the top surface of cover 50. Cover outer wall 51A has cover threads 59 which correspond with cup threads 26. As is common in the art of threaded containers, cap assembly 40 engages with cup 20 by means of turning cap assembly 40 relative to cup 20, or vice-versa. Cover outer wall 51A includes an array of cover ridges 52, that like cup ridges 29, provide increase friction with a user's hands during opening and thus reduced risk of spillage and contamination. To provide additional sealing, beyond that of standard container threads, is the existence and a tight clearance fit between inner wall 51B and cup inner wall surface 22. Together, and as shown in FIG. 8, wall 51B and cup surface 22 provide increased resistance to a fluid 80 from exiting or leaking from cup 20 over just threads.

Figure 6:
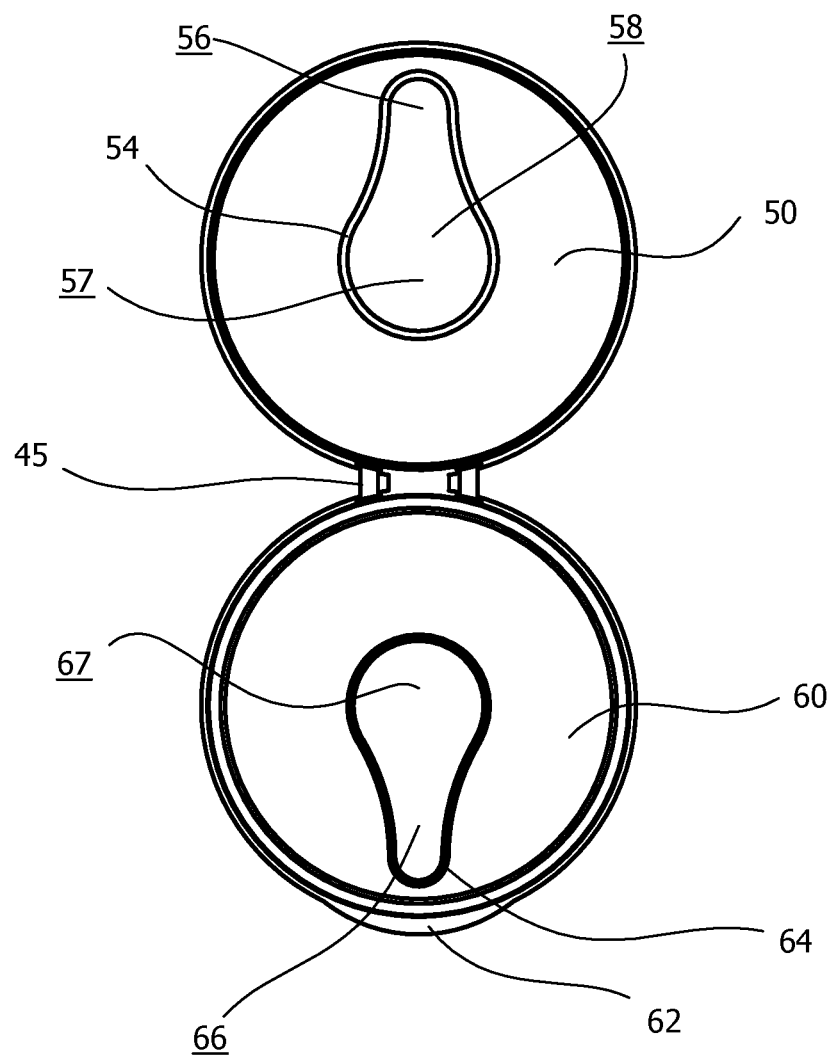
FIG. 6 is a top view of the cap assembly with the lid in the open position and showing its bottom surface.
Figure 15:
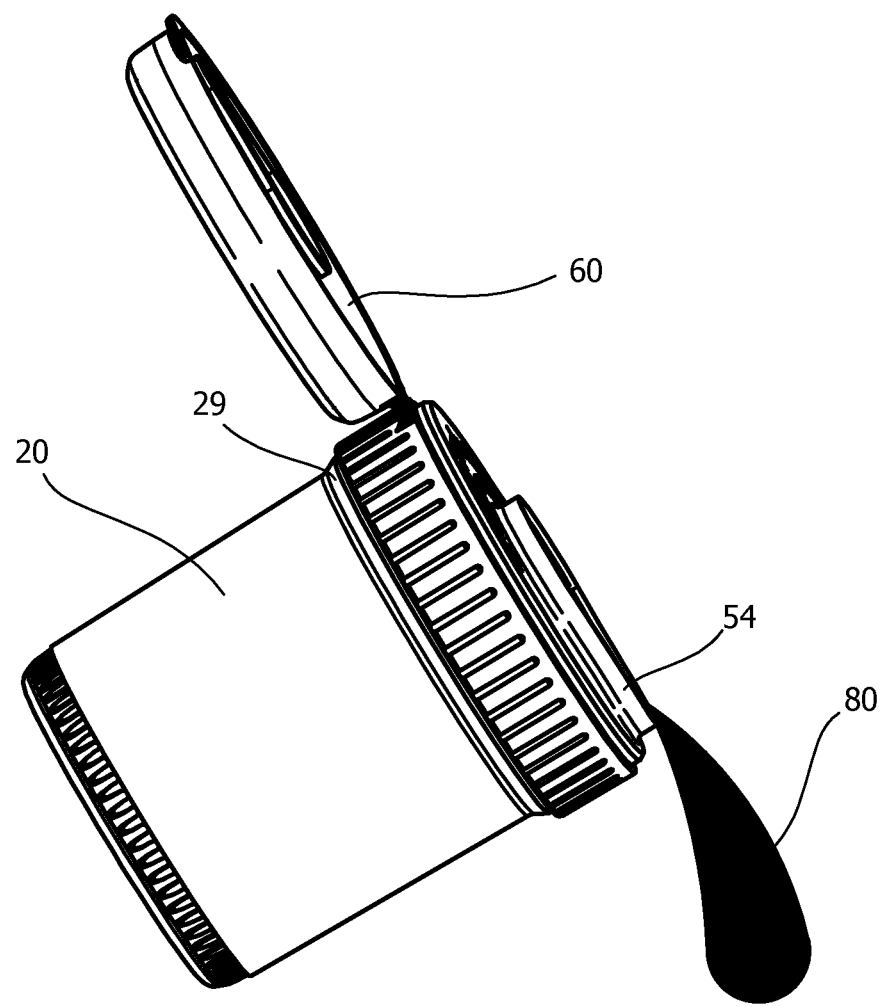
FIG. 15 is a side perspective view showing the specimen container system in a pouring position.
Figure 16:
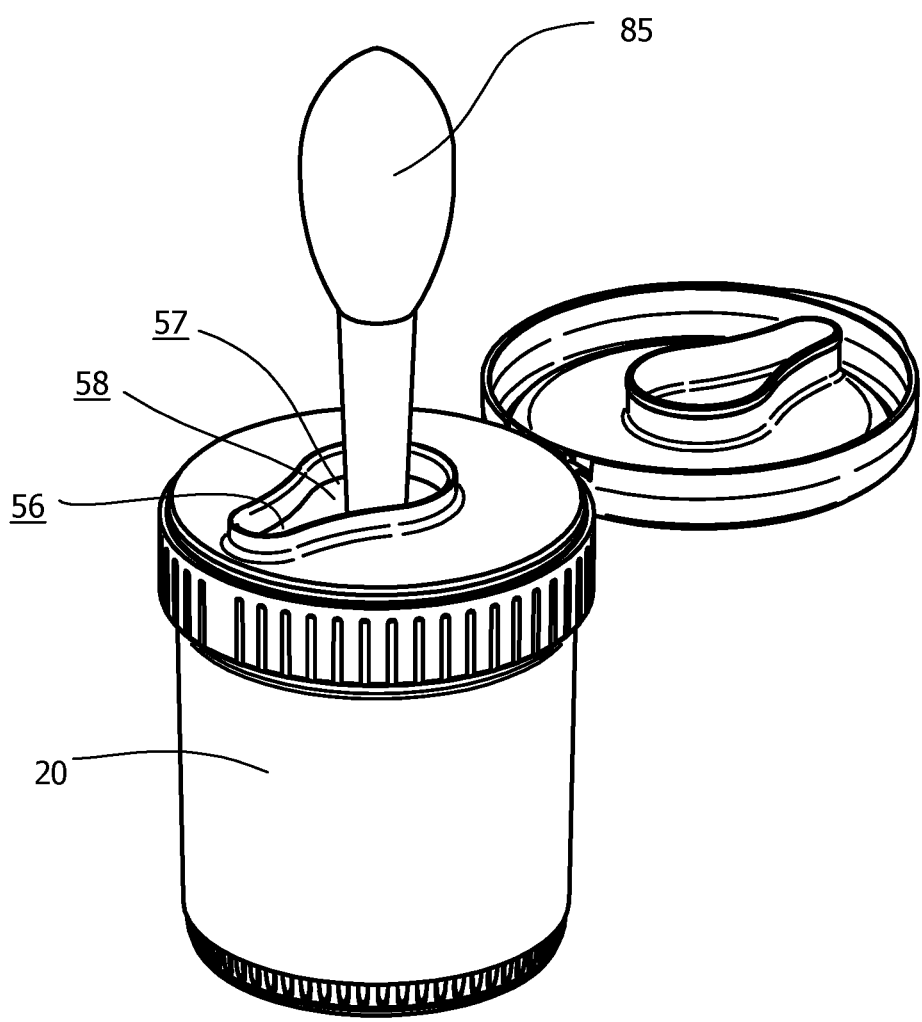
FIG. 16 is a top perspective view showing a withdrawal instrument extracting fluid from the specimen container system through the aperture of the cover.
Figure 19:
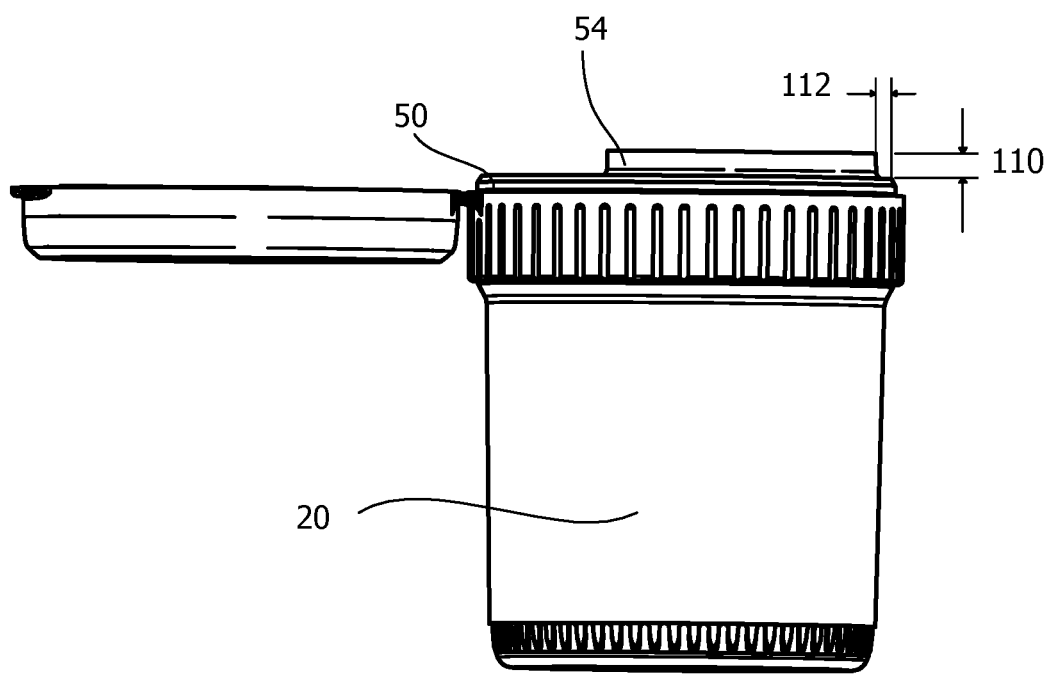
FIG. 19 is a side view of the specimen container of FIG. 1, and showing the height of the cover protrusion relative to its distance to the edge of the cup.

Extending through the top of cover 50 is aperture 58, which provides the means to access fluid 80 with cover 50 attached to cup 20 and with lid 60 in the open position. Surrounding aperture 58 is a cover protrusion 54 which extends upward from the top surface of cover 50 and creates a sealing surface with lid 60. Preferably, and as shown in FIG. 6, aperture 58 has a pouring section 56 and an access section 57. Although pouring section 56 and access section 57 may be any size or shape all within the spirit and scope of the present invention, as part of its best mode, pouring section 56 is narrower in diameter, or width, than access section 57. As shown in FIG. 19, cover protrusion 54 has a height 110 and is a distance 112 from the edge of cover 50. As shown in FIG. 15 wherein container system 10 is angled to pour liquid 80 out of pouring section 54 with reduced risk of drips contaminating of container system 10, height 110 is greater than distance 112. According to the best mode of the present invention but not limited to such, height 110 is approximately 3.4 millimeters and distance 112 is 2.5 millimeters. The size and shape of pouring section 56 may be optimized for a particular fluid, with the goal of creating optimal fluid velocity and a more predictable flow with less fluid turbulence than a larger opening. Cover protrusion 54 extends fluid 80 away from container system 10 when pouring, and provides a more predictable flow with less risk of contamination during the pouring process. Furthermore, the wider diameter of access section 57 ensures adequate airflow into container system 10 during the pouring process. Cover access section 57 is sized to provide access to pipettes and such for selectively removing fluid from container system 10 with lid 60 in the open position. FIG. 16 shows a pipette 85 inserted through access section 57 for extracting or withdrawing an amount of fluid 80. Wherein pipette 85 may be left inserted in access section 57 during the extraction or test process, the location of access section 57 through the center of cover 50 reduces the risk of accidental tipping of container system 10, spillage of fluid 80, and cross-contamination. Although a pipette is shown as an example fluid extraction instrument, other instruments are common in the art of laboratory testing, including a loop and syringe. The benefits of the present invention are not limited to any particular extraction or withdrawal instrument.

Figure 14:
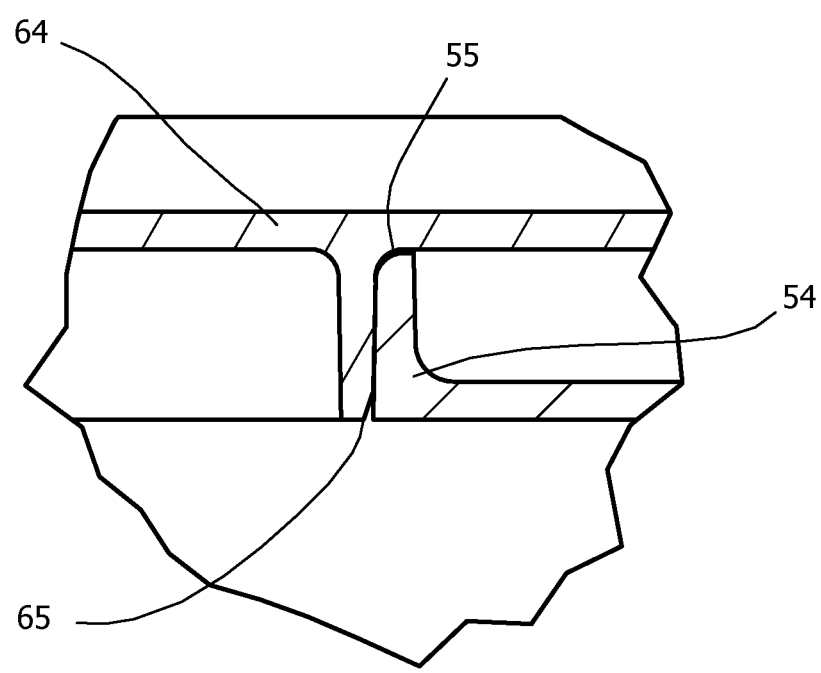
FIG. 14 is a detailed view of FIG. 8, and showing the cover protrusion creating a fluid tight seal with the protrusion of the lid. Both the cover and lid protrusions have a radius for facilitating closure of the lid to the cover.

Also shown in FIG. 1 is lid 60. A lid protrusion 64 extends downward from the bottom of lid 60 (as viewed in the closed position) and forms a seal with cover protrusion 54. As shown in FIG. 14, lid protrusion 64 extends inside of cover protrusion 54 and has a close tolerance fit as to restrict any leaks. Although lid protrusion 64 extends inside cover protrusion 54, an alternative embodiment may include having cover protrusion 54 extending inside of lid protrusion 64, or yet another embodiment may have two of lid protrusion 64, with one extending inside of cover protrusion 54 and the other lid protrusion 64 extending outside of cover protrusion 54. As shown in FIG. 14, the closure of cover protrusion 64 with lid protrusion 54 is facilitated with a lid protrusion lead-in 55 and a cover protrusion lead-in 65. Lead-ins 55 and 65 are radiuses that help align protrusions 54 and 64 during closing. The tight fit of lid protrusion 64 to cover protrusion 54 provides the means of sealing aperture 58. As shown in FIG. 6, lid protrusion 64 includes a lid pouring end 66 and a lid access end 67 which corresponds to the shape of cover protrusion 54 and aperture 58.

As best seen in FIG. 1, cover 60 includes a lip 62 which extends outwardly from cup 20 and cover 50. Lip 62 is in the general proximity opposite of hinge assembly 45 as to create a balanced opening force. Lip 62 provides the means for the user to easily lift up lid 60 from cover 50 in the closed position and for the user to access aperture 58 and liquid 80 within container system 10.

Figure 4:
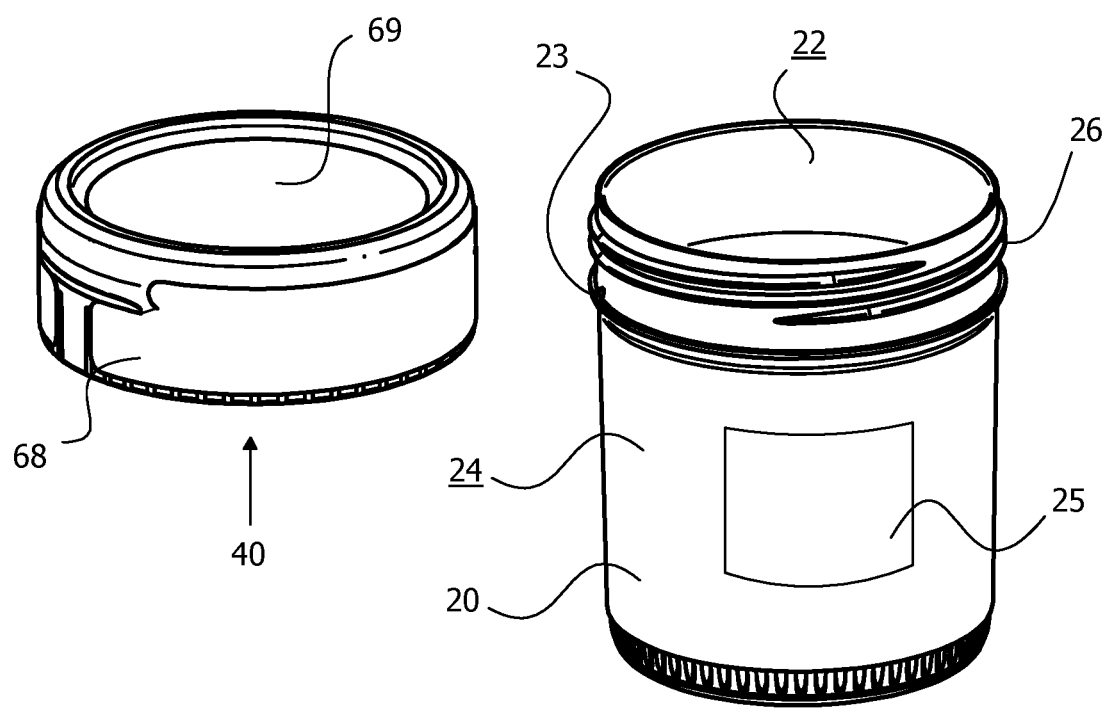
FIG. 4 is a top perspective view of the specimen container system and showing the cap assembly removed from the cup, and with the lid in the closed position with respect to the cover.

Traceability of specimen container system 10 is ensures test results correspond with the correct patient and test sample. As shown in FIG. 4, a lid label 69 is attached to the top of lid 60 and a cup label 25 is attached to cup 20. Both labels 69 and 25 may be any type of sticker that is preferably capable of being written on, and may contain pre-printed user instructions and warnings to the user.

A seal tape 68 is a sticker applied during the manufacturing process and is attached to both cover 60 and lid 50. Seal tape 68 is used to indicate if lid 50 has been moved from the closed to the open position. When opening lid 60, seal tape 68 splits with a partial amount remaining on lid 60 and a partial amount remaining on cover 50. Seal tape 68 provides the means of indicating to the lab if container system 20 has been compromised during transport.

Figure 17:
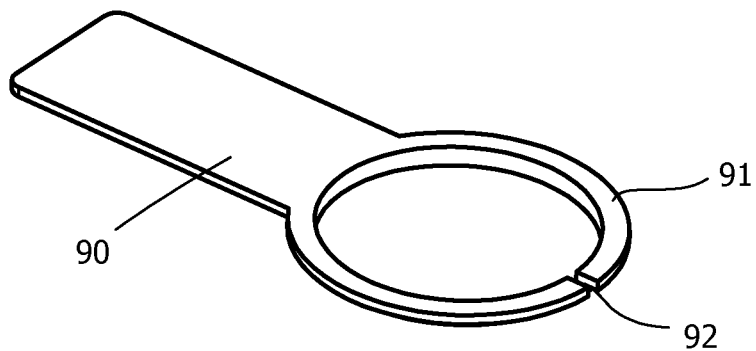
FIG. 17 is a perspective view of a cup holder.
Figure 18:
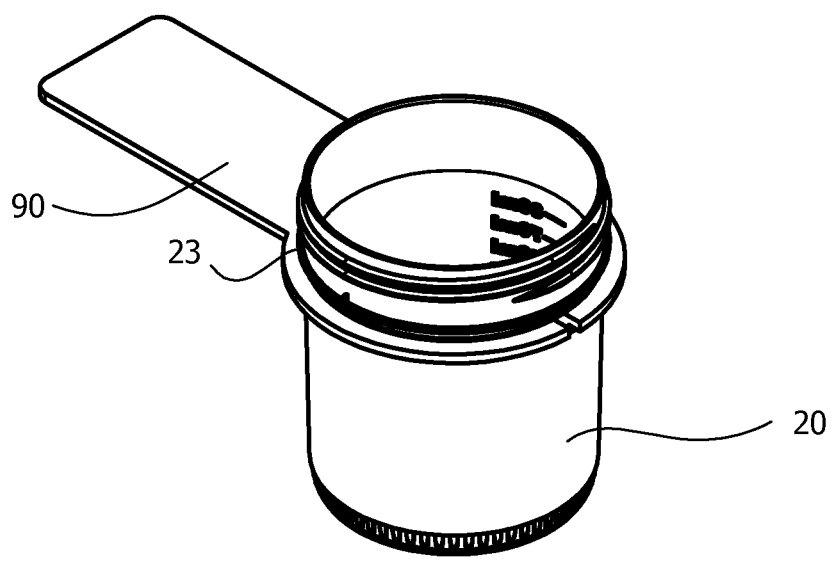
FIG. 18 is a perspective view the cup holder of FIG. 17 secured to the cup, for use in mid-stream fluid collection.

As previously described, cup 20 preferably includes cup shoulder 23 which extends around outer wall surface 24. As shown in FIGS. 17 and 18, cup shoulder 23 is used to control engagement of a holder 90. Holder 90 is used to capture mid-stream urine with reduced risk of contaminating the user's hands and potentially contaminating the outside surfaces of container system 10. Contamination of container system 10 increases the risk of cross-contamination of other containers. Holder 90 includes a ring section 91 that has a slightly smaller diameter than cup 20. Slit 92 allows ring section 91 to expand to the diameter of cup 20 thus creating a retaining force. Shoulder 23 keeps cup 20 from slipping out of holder 90 and further reduces risk of spillage, contamination and cross-contamination.

Figure 9:
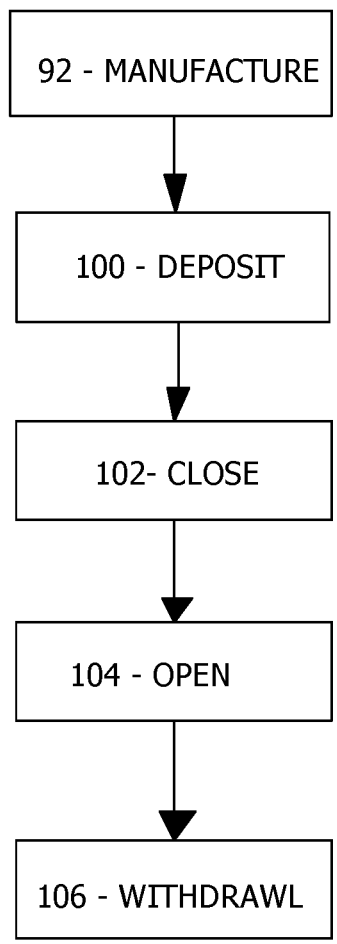
FIG. 9 is a process diagram showing the typical steps of using the present invention according to its best mode.
Figure 10:
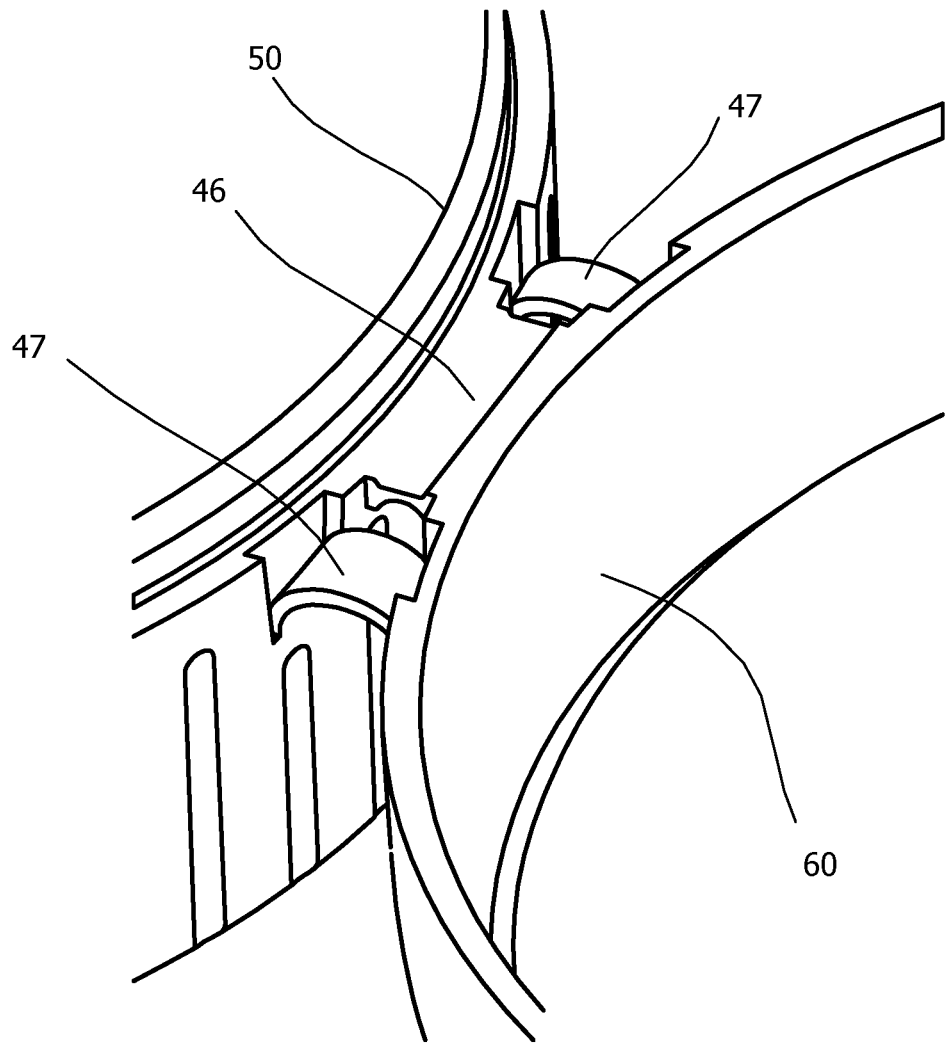
FIG. 10 is a partial perspective view of the preferred embodiment hinge assembly between the cover and the lid. The cover is shown open and exposing its bottom side, along with the living hinge and bias bands.

The use of specimen container system 10 as described herein is directed towards urine collection, transport and testing. This description is part of the best mode of the present invention, but the use of the present invention should not be construed to be limited to urine. The process for using specimen container system 10 is described in FIG. 9:

A manufacture step 92 is performed to create container system 10. Each component may be molded, or fabricated to the desired shape. Seal tape 68, lid label 69 and cup label 25 may be applied or shipped loose with container system 20. Furthermore, cap assembly 40 may be screwed to cup 20, or may also be shipped loose.

A deposit step 100 is the stage wherein a user deposits an amount of fluid within cup 20, either with or without holder 90. With cap assembly 40 removed from cup 20, a user places an amount of urine (fluid 80) into cup 20. This may be accomplished with a wide range of methods, including but limited to midstream urine capture techniques.

With fluid 80 inside of cup 20, the user or lab technician performs a close step 102 of sealing container system 10 by means of screwing cap assembly 40 to cup 20 with lid 60 in the closed position (lid 60 on top of cover 50). Specimen container system 10 may now be transported or stored until it is ready to be tested.

When ready to test, an open step 104 is performed by a tester to gain access to fluid 80. Unlike prior art system wherein the tester unscrews a cap from a container, potentially creating a contamination or spillage situation, with the present invention the tester simply lifts on lip 62 causing lid 60 to separate from cover 50. Hinge assembly 45 causes lid 60 to simply rotate away from cover 50 and to expose aperture 58. With limited open access between fluid 80 and the environment outside, there is less chance for cross-contamination between the two. In addition, with very little contact between the user and container system 10, there is little risk of contamination of fluid 80 by the hands or gloves of the tester. There is also little risk of the tester coming in contact with potentially biologically hazardous fluid 80. Furthermore, an unlike the prior art, if an accidental tipping of container system 10 occurs with lid 60 in the open position, cover 60 with aperture 58 will retain a portion of fluid 80 likely allowing the lab technician to perform the desired test without requiring another patient sample.

With lid 60 in the open position, the tester performs a withdrawal step 106. With lid 60 in the open position, bias bands 47 keep lid 60 in the open position, reducing the chance of lid 60 coming in accidental contact with a withdrawal instrument or impeding access to aperture 58. Bands 47 reduce the risk of contamination and cross-contamination during withdrawal step 106. The tester may tilt container system 10 and have fluid 80 travel through cover pouring section 56 and away from lid 60 via cover protrusion 54. The tester may also draw or transfer fluid 80 from container system 10 by inserting a pipette 85, or another withdrawal device, through aperture 58. Likely pipette 85, or drawing utensil, has a diameter greater than cover pouring section 56 and thus the utensil may be inserted through the larger sized access section 57. Cover pouring section 56 and cover access section 57 provide the means of both providing optimized pouring conditions and the ability to fit withdrawing utensils and to remove fluid 80 from container system 10 without having to separate cap assembly 40 from container 20.

The result of using novel specimen container system 10 is less risk of spilling fluid 80 during use, less risk of contamination and cross-contamination of fluid 80 causing diagnostic errors, and less risk of biological contamination of the user or tester "Infection Control", in comparison to the prior art. In addition, and as previously described, a tipped container system 10 is unlikely to require another patient sample due to cover 60 only exposing fluid 80 through aperture 58. Furthermore, in laboratories performing a large number of patient test, the novel method of separating lid 60 from cover 50 eliminates the need for the lab technician to unscrew containers which saves time and reduces risk of repetitive injuries such as carpal tunnel. The present invention is designed for the safety and adherence to "Universal Precautions" as mandated by the Center for Disease Control for microbiologists.

Figure 20:
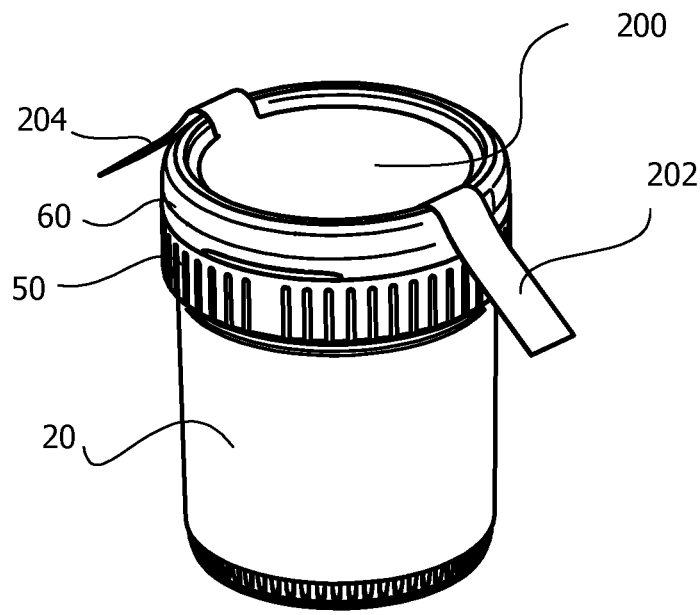
FIG. 20 is a top perspective view of an alternative embodiment lid seal label prior to the flaps being fastened to the cup.
Figure 21:
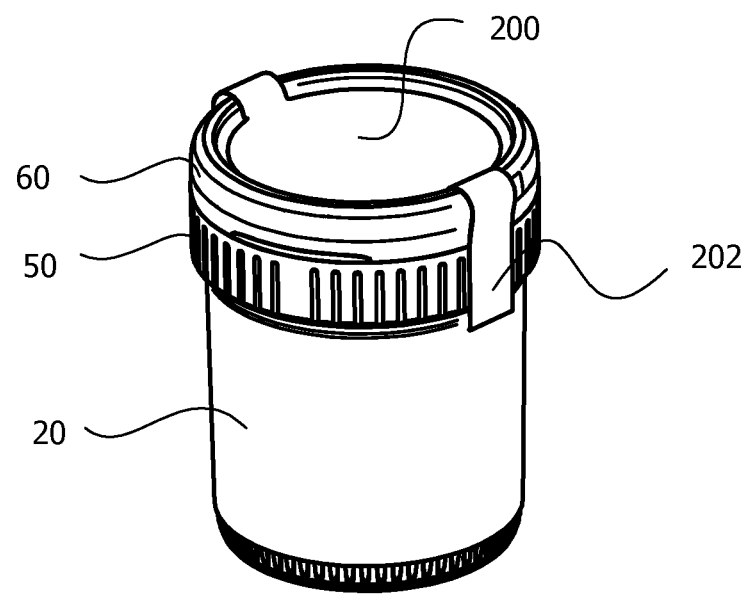
FIG. 21 is a top perspective view of the alternative embodiment lid seal label of FIG. 20, with the flaps being fastened to the cup.

Other embodiments exist within the spirit and scope of the present invention. FIG. 20 and FIG. 21, show an alternative method for providing a tamper resistant seal between the cover, lid and cup. A tamper resistant lid label 200 is shown secured, preferably with adhesive, to lid 60. As shown in FIG. 20, one or more label flaps 202 are shown in the unsecured state, by having an adhesive cover 204 covering the sticky side (closest to cup 20) of flaps 202. By having flaps 202 in the open position, deposit step 100 may be accomplished as previously described with cap assembly 40 free to twist off from cup 20. After deposit step 100 is complete, the user or practitioner removes adhesive cover 204 on one or more flaps 202 to expose the adhesive. The user or practitioner then applies a force to flaps 202 to make label 200 adhere to cover 50. Alternatively, lid label 200 may be adhered to lid 60, cover 50 and cup 20. Prior to testing, lid 60 is rotated from cover 50 to the open position and flaps 202 tear from lid label 200 indicating fluid 80 has been accessed. Although two of flaps 202 are shown, it should be appreciated that any number will provide the means to indicate specimen container system 10 has been opened.

Figure 22:
FIG. 22 is a perspective view of a seal member as part of the alternative embodiment of FIG. 23.
Figure 23:
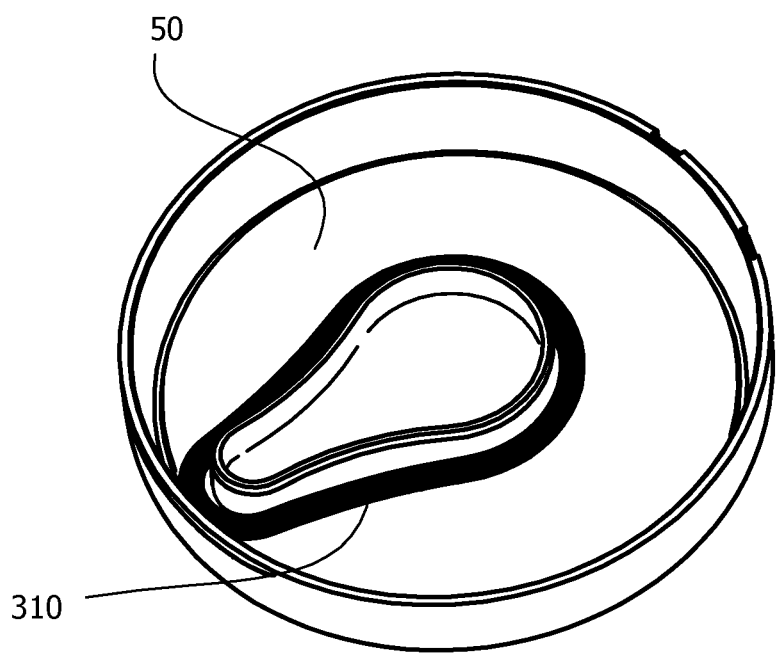
FIG. 23 is bottom perspective view of the seal member of FIG. 22 placed onto the protrusion of the bottom side of the lid.

Yet another embodiment is shown in FIG. 22 and FIG. 23. A seal member 310 is preferably an o-ring type member that is molded in the general shape of protrusion 64 of lid 60. As shown in FIG. 23, seal member 310 is placed around the outside of protrusion 64 and by making seal member 310 just smaller than the outside surface of protrusion 64, a compression fit may be obtained. With lid 60 is in the closed position, seal member makes contact with both lid 60 and cover 50. It should be appreciated that although seal member 310 is preferably a secondary item that is placed onto protrusion 64, seal member 310 may be co-molded with lid 60 or deposited as liquid onto lid 60 and allowed to cure into the desired shape. Seal member 310 provides the means of producing increased sealing between lid 60 and cover 50 which may be desirable for use in particular applications.

While the specimen container system herein described constitute preferred embodiments of the invention, it is to be understood that the invention is not limited to these precise form of assemblies, and that changes may be made therein without departing from the scope and spirit of the invention.

I claim:

1. A specimen container system comprising:
    a cup having a cup bottom and a cup side wall, said cup side wall having a cup inside surface and a cup seal thread opposite to said cup bottom;
    a cover having a top wall connected to a cover side wall, said cover side wall having a cover seal thread for engaging with said cup seal thread and maintaining said top wall above said cup seal thread, said top wall having an aperture comprised of a pour section and an access section, wherein said pour section has a width less than said access section and further wherein said pour section is closer to said cover side wall than said access section and said access section is aligned with a center of said cover, said aperture having a cover protrusion extending upward from said top wall around the perimeter of said aperture, said cover protrusion having a height above said cover side wall greater than a minimum distance between said cover protrusion and said cover side wall, wherein said cover includes an inner cover wall in contact with said cup inside surface;
    a lid having a base, said base having a lid protrusion;
    a withdrawal instrument extending through said access section and at least partially within said cup, said withdrawal instrument having an instrument width greater than said pour section and said instrument width being less than said access section;
    a hinge connecting said lid to said cover side wall; and, wherein said lid protrusion creates a slip fit with said cover protrusion.

2. The specimen container system of claim 1, wherein said cover protrusion includes a lead-in radius along its entire perimeter for engaging with said lid protrusion.

3. The specimen container system of claim 1, wherein said hinge includes at least one biasing band mechanism in direct connection with both said lid and said cover for maintaining said lid in an open position.

4. The specimen container system of claim 1, wherein a seal tape is attached to said lid and said cover.

5. The specimen container system of claim 1, further comprising a seal member connected to said lid protrusion and in contact with said cover protrusion.

6. The specimen container system of claim 1, wherein said lid includes a tab that extends outward of said cup side wall when said lid is in a closed position.

7. The specimen container system of claim 1, wherein said cup includes a cup shoulder located between said cup bottom and said cup seal thread and wherein said cup shoulder has a diameter greater than said cup side wall.

8. A specimen container system comprising:
a cup having a bottom and a cup sidewall, said cup sidewall having a cup treaded section opposite to said bottom;
a cover having a base and a cover sidewall, said cover sidewall having a cover treaded section, said base having an aperture comprised of an access section and a connected pour section within a plane of said base, said aperture having a cover protrusion extending from said base to above said cover sidewall and surrounding said aperture, said cover protrusion having a height above said cover sidewall and a distance from said cup sidewall, wherein said height is greater than said distance, wherein said cover includes a cover inner wall in contact with a cup inside surface;
further wherein said access section has a width greater than said pour section and said pour section and said access section are directly accessible to said bottom of said cup;
a withdrawal instrument extending through said access section and at least partially within said cup, said withdrawal instrument having an instrument width greater than said pour section and said instrument width being less than said access section; and,
a lid rotationally constrained to said cover by a hinge, and said lid having a lid protrusion in a slip fit with said cover protrusion.

9. The specimen container system of claim 8, further including a seal member in direct contact with said lid protrusion.

10. The specimen container system of claim 8, wherein said hinge includes at least one biasing band in direct connection with both said lid and said cover for maintaining said lid in an open position, said open position having said lid substantially parallel to said base.

11. The specimen container system of claim 8, wherein a seal tape is attached to said lid and said cover.

12. The specimen container system of claim 8, wherein said access section is at least twice the width of said first pour section.

13. The specimen container system of claim 8, wherein said lid includes a tab that extends outward of said cup side wall when said lid is in a closed position.

14. The specimen container system of claim 8, wherein said cup includes a cup shoulder located between said bottom and said cup treaded section and wherein said cup shoulder has a diameter greater than said cup side wall.

15. A specimen container system comprising:
a cup having a bottom and a cup sidewall, said cup sidewall having a cup treaded section opposite to said bottom and a plurality of fluid level indicators;
a cover having a base and a cover sidewall, said cover sidewall having a cover treaded section, said base having an aperture comprised of an access section and a pour section, said aperture having a cover protrusion surrounding said aperture and extending from said base to above said cover sidewall, said cover protrusion having a height above said cover sidewall and a radial distance from said cup sidewall wherein said height is greater than said radial distance and said radial distance is less than 20 percent of a diameter of said cup, wherein said cover includes a cover inner wall in close proximity to an inner surface of said cup and wherein said cup shoulder has a diameter greater than said cup side wall;
further wherein said access section has a width greater than said pour section;
a withdrawal instrument extending through said access section and at least partially within said cup, said withdrawal instrument having an instrument width greater than said pour section and said instrument width being less than said access section;
a lid rotationally constrained to said cover sidewall by a hinge having one or more bias bands for moving said lid from a closed position and an open position, said open position having said lid substantially parallel to said base, said lid having a continuous protrusion for creating a slip fit with said cover protrusion; and,
a tamper label in contact with said cover and said lid.

16. The specimen container system of claim 15, wherein said lid includes a seal member in direct contact with said lid protrusion.

17. The specimen container system of claim 15, wherein said lid includes a lid label.

\* \* \* \* \*